United States Patent [19]

Ishizaka et al.

[11] Patent Number: 5,122,343
[45] Date of Patent: Jun. 16, 1992

[54] BIOCHEMICAL ANALYSIS APPARATUS WITH AN INTEGRAL CENTRIFUGE

[75] Inventors: Hideo Ishizaka; Yukihide Miyata, both of Kanagawa; Yoshio Saito, Saitama; Kiyoshi Yamada, Tokyo, all of Japan

[73] Assignee: Fuji Photo Film Co., Ltd., Kanagawa, Japan

[21] Appl. No.: 617,293

[22] Filed: Nov. 19, 1990

Related U.S. Application Data

[60] Continuation of Ser. No. 420,407, Oct. 12, 1989, abandoned, which is a division of Ser. No. 218,398, Jul. 13, 1988, abandoned.

[30] Foreign Application Priority Data

| Jul. 15, 1987 | [JP] | Japan | 62-176564 |
| Jul. 15, 1987 | [JP] | Japan | 62-176565 |
| Sep. 24, 1987 | [JP] | Japan | 62-239860 |
| Sep. 24, 1987 | [JP] | Japan | 62-239861 |

[51] Int. Cl.$^5$ .................. G01N 21/01; G01N 35/00
[52] U.S. Cl. .................... 422/66; 422/63; 422/64; 422/65; 422/67; 436/44
[58] Field of Search ............. 422/63-67; 436/44, 46

[56] References Cited

U.S. PATENT DOCUMENTS

| 3,526,480 | 9/1970 | Findl et al. ............... 435/4 |
| 3,728,081 | 4/1973 | Bidanset .................. 422/66 |
| 4,071,315 | 1/1978 | Chateau .................. 422/66 |
| 4,272,482 | 6/1981 | Jessop et al. ............ 422/66 X |
| 4,279,514 | 7/1981 | Blümel et al. ........... 356/445 |
| 4,298,570 | 11/1981 | Lillig et al. ............. 422/64 |
| 4,327,073 | 4/1982 | Huang ................... 422/66 X |
| 4,512,952 | 4/1985 | Blanding et al. ......... 422/64 |
| 4,708,940 | 11/1987 | Yoshida et al. .......... 422/72 |
| 4,764,342 | 8/1988 | Kelln et al. ............. 422/72 |
| 4,798,705 | 1/1989 | Jakubowicz et al. ..... 422/63 |
| 5,039,615 | 8/1991 | Takahata ............... 422/63 X |

Primary Examiner—James C. Housel
Assistant Examiner—Arlen Soderquist
Attorney, Agent, or Firm—Sughrue, Mion, Zinn, Macpeak & Seas

[57] ABSTRACT

A biochemical analysis apparatus includes a sample accommodating region, an accommodating region for test films containing a reagent which reacts with a liquid sample to give rise to a change in optical density, and a conveyor for sequentially pulling out each test film from the test film accommodating region. An applicator takes up the liquid sample fromt he sample accommodating region and applies it to the test film at the position to which the test film has been pulled out. An incubator incubates the sample-applied film portion for a predetermined time, and a detector measures the optical density of the sample applied applied film portion during or after the passage of the predetermined time. The conveyor, the incubator and the detector are provided to correspond to each of the test films, and a movement device moves the applicator to apply the liquid sample to the test films.

12 Claims, 8 Drawing Sheets

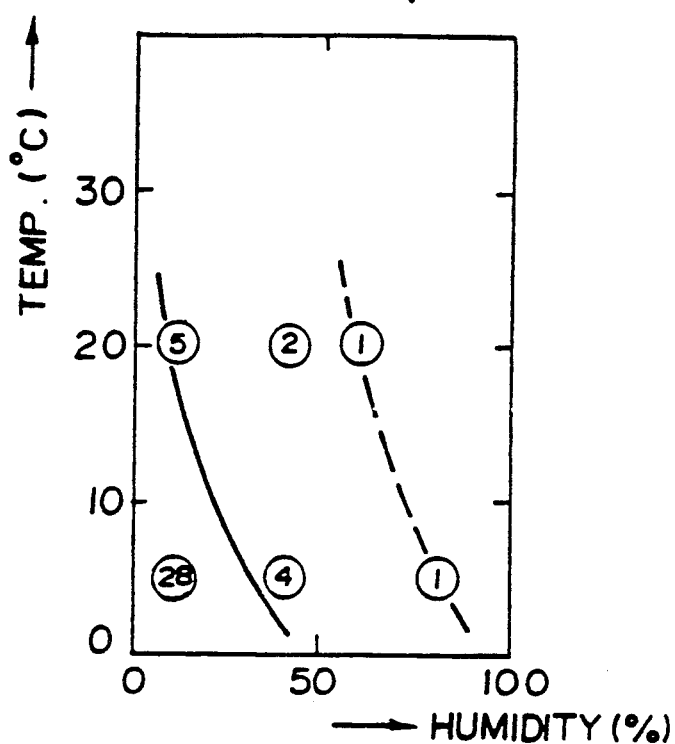
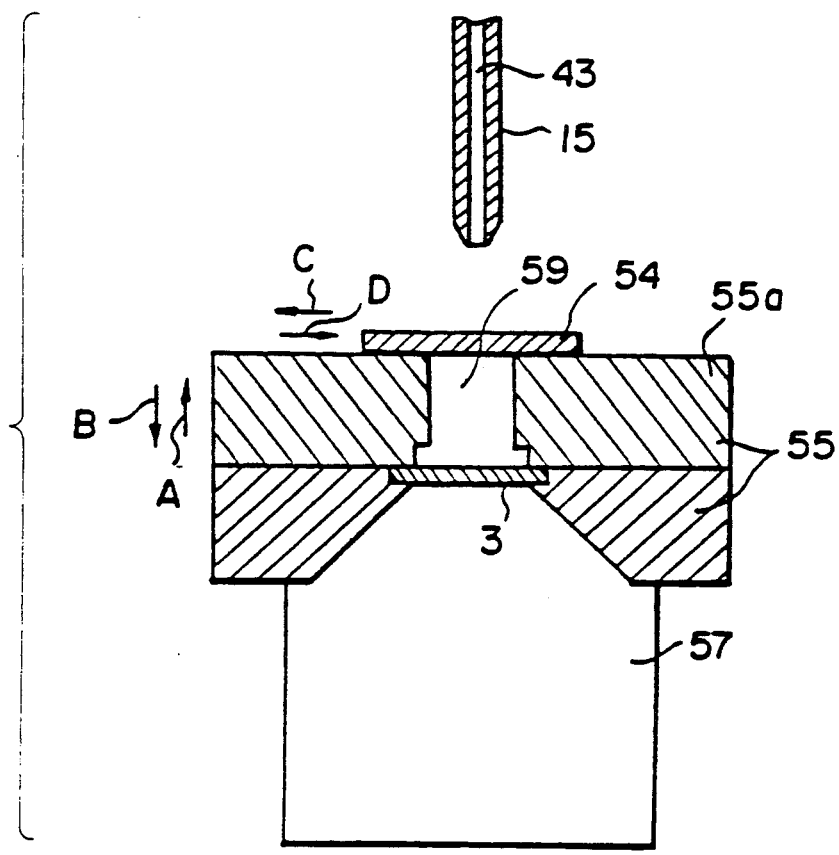

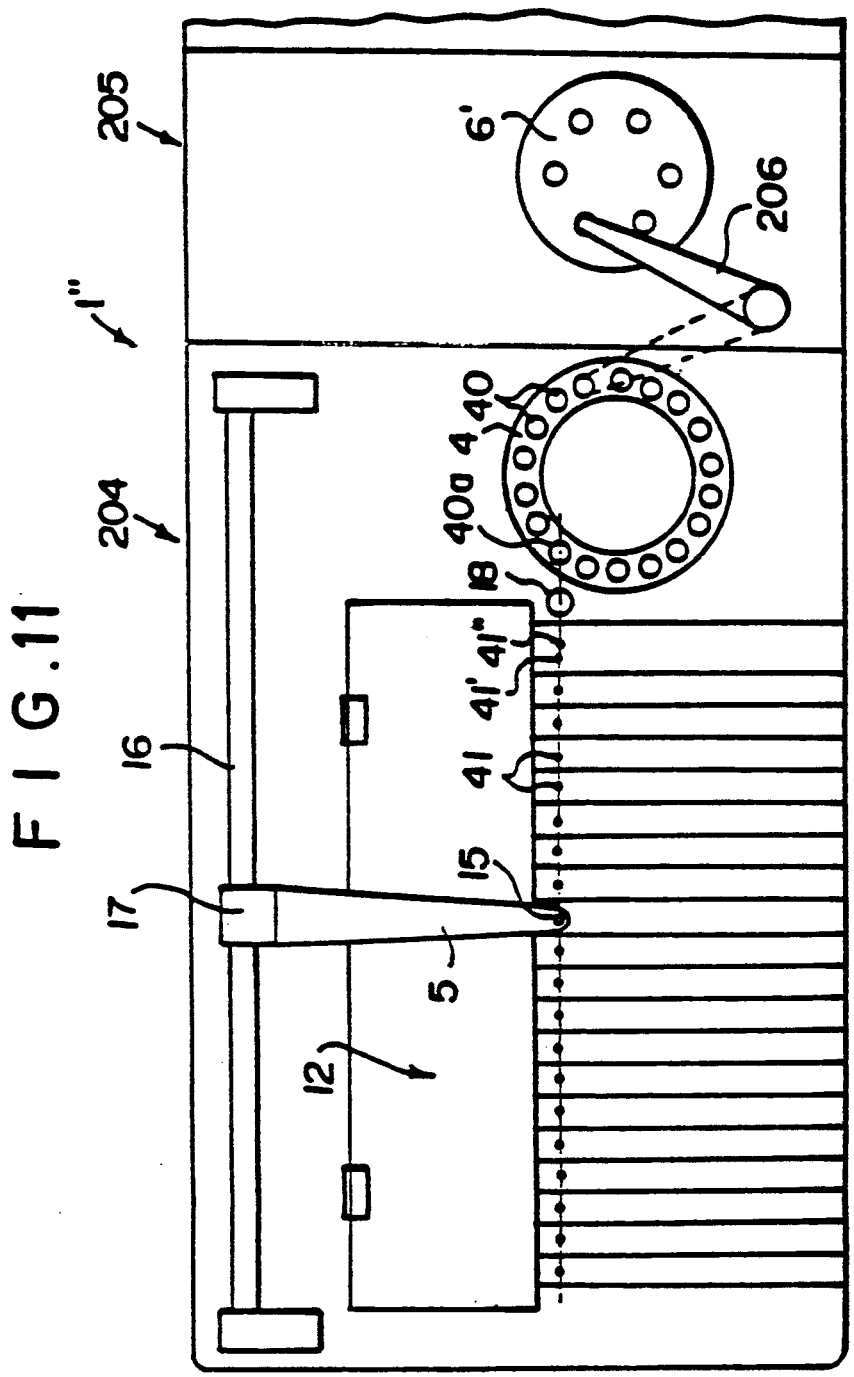

BIOCHEMICAL ANALYSIS APPARATUS WITH AN INTEGRAL CENTRIFUGE

This is a continuation of application No. 07/420,407 filed Oct. 12, 1989 now abandoned, which was a division of application Ser. No. 07/218,398, now abandoned, filed Jul. 13, 1988.

BACKGROUND OF THE INVENTION

1. Field of the Invention

This invention relates to a biochemical analysis apparatus for applying a liquid sample to a test film provided with a single reagent layer or a plurality of reagent layers, maintaining the test film at a predetermined temperature (i.e. carrying out incubation) for a predetermined time, and measuring the degree of reaction of the reagent with the liquid sample during or after the incubation.

2. Description of the Prior Art

Qualitative or quantitative analysis of a specific chemical constituent in a liquid sample is generally conducted for various industrial purposes. Particularly, it is very important in biochemical and clinical fields to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55(1980)-164356, there has been developed and put into practice a dry type chemical analysis slide for quantitatively analyzing a specific chemical constituent or a specific physical constituent contained in a liquid sample simply by applying a droplet of the liquid sample. With the chemical analysis slide, it is possible to analyze a liquid sample more simply and more quickly than with the conventional wet type analysis method. Therefore, the use of the chemical analysis slide is desirable particularly in medical organizations, research laboratories, or the like where many samples are to be analyzed.

In order to analyze a chemical constituent or the like contained in a liquid sample by use of the chemical analysis slide, a measured amount of the liquid sample is put on the chemical analysis slide and is maintained at a predetermined temperature (i.e. incubated) for a predetermined time in an incubator to cause a color reaction. The chemical analysis slide is then exposed to measuring light having a wavelength selected in advance in accordance with the combination of the constituent of the liquid sample with a reagent contained in the reagent layer of the chemical analysis slide, and the light reflected by the chemical analysis slide is measured in terms of the optical density. In this manner, it is possible to achieve quantitative analysis of the chemical constituent or the like.

In the medical organizations, research laboratories or the like in which many liquid samples are to be analyzed, it is desirable that the analysis be conducted automatically and sequentially. To satisfy this need, there have been proposed various chemical analysis apparatuses for carrying out sample analysis automatically and sequentially by use of the aforesaid chemical analysis slides. One of such chemical analysis apparatuses is disclosed in, for example, Japanese Unexamined Patent Publication No. 56(1981)-77746. Also, as a means for analyzing liquid samples automatically and sequentially, there has been proposed in, for example, U.S. Pat. No. 3,526,480 an apparatus wherein a long tape-like test film containing a reagent is accommodated instead of the aforesaid chemical analysis slides, and sample application, incubation and measurement are carried out sequentially by pulling out the test film.

With the technique wherein a single chemical analysis slide is used for a single measurement, many chemical analysis slides must be processed for automatically and sequentially carrying out the analysis of liquid samples, and therefore the apparatus becomes complicated, large and expensive. On the other hand, the technique wherein the long tape-like test film containing a reagent is used instead of the chemical analysis slide is advantageous for carrying out measurement automatically and sequentially. However, with the aforesaid conventional apparatus wherein a plurality of the long test films are stacked one upon another and conveyed along nearly the same path, the respective long test films are provided with openings for the purposes of, for example, allowing sample application to a long test film located at a lower part of the stack and preventing the long test films other than the long test film which is being subjected to measurement from obstructing the measurement. As the long test films must be processed for the provision of the openings, the cost increases, the number of measurement operations possible with a single long test film decreases, and the running cost of the apparatus increases. Also, in order to prevent interference of the respective long test films with one another at the time of the sample application, the measurement and other steps, conveyance of the long test films must be controlled in a complicated manner for conveying the long test films in good sequence.

SUMMARY OF THE INVENTION

The primary object of the present invention is to provide a biochemical analysis apparatus which is made simple, small and cheap by employing the system utilizing a long tape-like test film advantageous for carrying out measurement automatically and sequentially, which reduces the running cost by elimination of processing for the provision of an opening in the long test film, and which simultaneously carries out measurement of a plurality of measurement items.

Another object of the present invention is to provide a biochemical analysis apparatus, which automatically and sequentially carries out operations from a step of accommodating body fluid prior to the preparation of a liquid sample and preparing the liquid sample from the body fluid to a step of analysis of the prepared liquid sample, thereby to increase the operating efficiency and minimizing the possibility of a sample processing error arising when a plural kinds of body fluids (liquid samples) are processed simultaneously.

A further object of the present invention is to provide a biochemical analysis apparatus which carries out measurement of a plurality of measurement items simultaneously and quickly.

A still further object of the present invention is to provide a biochemical analysis apparatus which has a simple mechanism, thereby to minimize operation failures and reduce the cost, and which has a configuration suitable for quick processing.

The present invention provides a first biochemical analysis apparatus comprising:

i) a sample accommodating means for accommodating a liquid sample, ii) a test film accommodating means for accommodating a long test film containing a reagent which reacts with said liquid sample to give rise to a change in optical density, iii) a test film conveyance means for sequentially pulling out said long test film accommodated in said test film accommodating means, iv) a sample application means for taking up said liquid sample accommodated in said sample accommodating means and applying a predetermined amount of said liquid sample onto said long test film at the position to which said long test film has been pulled out of said test film accommodating means, v) an incubator for maintaining the sample-applied portion of said long test film at a predetermined temperature for a predetermined time, and vi) a detection means for irradiating light to said sample-applied portion of said long test film and measuring the optical density given rise to by said reaction during or after the passage of said predetermined time, wherein said test film accommodating means is constituted to accommodate a plurality of the long test films, said test film conveyance means, said incubator and said detection means are provided to correspond to each of a plurality of said long test films, and a movement means is provided for moving said sample application means so as to carry out the sample application to the predetermined position on each of a plurality of said long test films.

The present invention also provides a second biochemical analysis apparatus comprising:

i) a sample accommodating means for accommodating a liquid sample, ii) a centrifugation means for accommodating body fluid and preparing a liquid sample by centrifugation of the body fluid, iii) a sample transfer means for transferring said liquid sample prepared by said centrifugation means to said sample accommodating means, iv) a test film accommodating means for accommodating a test film reacting with said liquid sample to give rise to a change, v) a test film conveyance means for sequentially conveying said test film accommodated in said test film accommodating means to a predetermined position outside of said test film accommodating means, vi) a sample application means for taking up said liquid sample out of said sample accommodating means and applying a predetermined amount of said liquid sample onto said test film conveyed to said predetermined position, vii) an incubator for maintaining the sample-applied portion of said test film at a predetermined temperature for a predetermined time, and viii) a detection means for measuring a change at said sample-applied portion of said test film during or after the passage of said predetermined time.

The present invention further provides a third biochemical analysis apparatus comprising:

i) a sample accommodating means for accommodating a liquid sample, ii) a centrifugation means for accommodating body fluid and preparing a liquid sample by centrifugation of the accommodated body fluid, iii) a test film accommodating means for accommodating a test film reacting with said liquid sample to give rise to a change, iv) a test film conveyance means for sequentially conveying said test film accommodated in said test film accommodating means to a predetermined position outside of said test film accommodating means, v) a sample application means for taking up said liquid sample out of one of said sample accommodating means and said centrifugation means selectively and applying a predetermined amount of said liquid sample onto said test film conveyed to said predetermined position, vi) an incubator for maintaining the sample-applied portion of said test film at a predetermined temperature for a predetermined time, and vii) a detection means for measuring a change at said sample-applied portion of said test film during or after the passage of said predetermined time.

The present invention still further provides a fourth biochemical analysis apparatus comprising:

i) a sample accommodating means for accommodating a liquid sample and provided with a centrifuging function for accommodating body fluid and preparing a liquid sample by centrifugation of the accommodated body fluid, ii) a test film accommodating means for accommodating a test film reacting with said liquid sample to give rise to a change, iii) a test film conveyance means for sequentially conveying said test film accommodated in said test film accommodating means to a predetermined position outside of said test film accommodating means, iv) a sample application means for taking up said liquid sample out of said sample accommodating means and applying a predetermined amount of said liquid sample onto said test film conveyed to said predetermined position, v) an incubator for maintaining the sample-applied portion of said test film at a predetermined temperature for a predetermined time, and vi) a detection means for measuring a change at said sample-applied portion of said test film during or after the passage of said predetermined time.

The present invention also provides a fifth biochemical analysis apparatus comprising:

i) a sample accommodating means for accommodating a liquid sample, ii) a test film accommodating means for accommodating a test film reacting with said liquid sample to give rise to a change, iii) a test film conveyance means for sequentially conveying said test film accommodated in said test film accommodating means to a predetermined position outside of said test film accommodating means, iv) a sample application means for taking up said liquid sample accommodated in said sample accommodating means and applying a predetermined amount of said liquid sample onto said test film conveyed to said predetermined position, v) an incubator for maintaining the sample-applied portion of said test film at a predetermined temperature for a predetermined time, and vi) a detection means for measuring a change at said sample-applied portion of said test film, wherein said test film accommodating means is constituted to accommodate a plurality of the test films different in their measurement items from one another in parallel, and said sample application means is constituted to be capable of accommodating said liquid sample in an amount necessary for the sample application to all of the test films, that correspond to a necessary measurement item among a plurality of the measurement items, at one time, and to apply said liquid sample sequentially onto said test films corresponding to said necessary measurement item.

The present invention further provides a sixth biochemical analysis apparatus comprising:

i) a sample accommodating means for accommodating a liquid sample, ii) a test film accommodating means for accommodating a test film reacting with said liquid sample to give rise to a change, iii) a test film conveyance means for sequentially conveying said test film accommodated in said test film accommodating means to a predetermined position outside of said test film accommodating means, iv) a sample application means for taking up said liquid sample out of said sample accommodating means and applying a predetermined amount of said liquid sample onto said test film conveyed to said predetermined position, v) an incubator for maintaining the sample-applied portion of said test film at a predetermined temperature for a predetermined time, and vi) a detection means for measuring a change at said sample-applied portion of said test film during or after the passage of said predetermined time, wherein said test film accommodating means is constituted to accommodate a plurality of the test films, said sample application means is provided with a sample applying nozzle moveable along a straight line or a circular arc, and the liquid sample take-out position at which said liquid sample is taken up by said sample application means and all of the sample applying positions at which said liquid sample is applied onto a plurality of said test films are disposed on the straight line or the circular arc corresponding to the movement path of said sample applying nozzle.

The term "test film" used herein for the second to sixth biochemical analysis apparatuses in accordance with the present invention embraces an electrolyte determination slide (which is used for quantitatively analyzing the ionic activity in a liquid sample by applying the liquid sample and a reference solution to the slide, incubating the slide, and then measuring a difference in potential corresponding to the difference in ionic activity between the liquid sample and the reference solution), a chemical analysis slide, and a long tape-like test film employed instead of the chemical analysis slide.

With the first biochemical analysis apparatus in accordance with the present invention wherein the test film accommodating means is constituted to accommodate a plurality of the long test films, and the test film conveyance means, the incubator and the detection means are provided to correspond to each of a plurality of said long test films, the long test films need not be processed for the provision of openings, and the running cost can be reduced. Also, as the movement means is provided for moving the sample application means so as to carry out the sample application to the predetermined position on each of a plurality of the long test films, measurement of a plurality of measurement items can be carried out simultaneously by accommodating the long test films for a plurality of the measurement items in the test film accommodating means.

Also, with the first biochemical analysis apparatus in accordance with the present invention, the test film accommodating means for accommodating the long test films each containing a reagent which reacts with the liquid sample to give rise to a change in optical density, and controlling the unused portions of the long test films at a predetermined temperature and humidity is provided. Each long test film accommodated in the test film accommodating means is sequentially pulled out by the test film conveyance means, and the liquid sample accommodated in the sample accommodating means is taken up by the sample application means and applied onto the long test film at the position to which the long test film has been pulled out of the test film accommodating means. Thereafter, the sample-applied portion of the long test film is incubated, the optical density of the incubated portion of the long test film is measured by the detection means. Therefore, a change in the optical density produced by the color reaction can be measured automatically and sequentially, and the biochemical analysis apparatus can be made simple, small and cheap. Also, in the case where the long test film is not used over its overall length in a series of measurements and a film portion remains unused, the remaining unused portion of the test film can be stored in the biochemical analysis apparatus such that the remaining unused portion does not deteriorate and is usable for the next measurement.

With the second biochemical analysis apparatus in accordance with the present invention wherein the centrifugation means is provided, the liquid sample can be prepared from body fluid The liquid sample thus prepared is automatically transferred by the sample transfer means to the sample accommodating means, taken out of the sample accommodating means, applied onto the test film, incubated and then subjected to the measurement. Therefore, the operations from the step of preparing the liquid sample from the body fluid to the step of analysis of the prepared liquid sample can be carried out automatically and sequentially, the operating efficiency can be increased, and a sample processing error arising when plural kinds of body fluids (liquid samples) are processed simultaneously can be minimized.

With the third biochemical analysis apparatus in accordance with the present invention, instead of providing the sample transfer means in the second biochemical analysis apparatus in accordance with the present invention, the sample application means is constituted to take out the liquid sample from one of the sample accommodating means and the centrifugation means selectively. Therefore, as in the case of the second biochemical analysis apparatus in accordance with the present invention, the operations from the step of preparing the liquid sample from the body fluid to the step of analysis of the prepared liquid sample can be carried out automatically and sequentially, the operating efficiency can be increased, and a sample processing error arising when plural kinds of body fluids (liquid samples) are processed simultaneously can be minimized.

With the fourth biochemical analysis apparatus in accordance with the present invention wherein, instead of providing the centrifugation means independently of the sample accommodating means as in the second and third biochemical analysis apparatuses, the sample accommodating means provided with the centrifuging function is employed. Therefore, as in the case of the second and third biochemical analysis apparatuses in accordance with the present invention, the operations from the step of preparing the liquid sample from the body fluid to the step of analysis of the prepared liquid sample can be carried out automatically and sequentially, the operating efficiency can be increased, and a sample processing error arising when plural kinds of body fluids (liquid samples) are processed simultaneously can be minimized.

With the fifth biochemical analysis apparatus in accordance with the present invention, the test film accommodating means is constituted to accommodate a plurality of the test films different in their measurement items from one another in parallel, and the sample application means is constituted to be capable of accommodating the liquid sample in an amount necessary for the sample application to all of the test films, that correspond to a necessary measurement item among a plurality of the measurement items, at one time, and to apply the liquid sample sequentially onto the test films corresponding to the necessary measurement item. Therefore, the operation of accommodating the liquid sample in the sample application means need not be repeated for each measurement item. Also, as the test films are accommodated in parallel, control for conveying the test films is simplified. Accordingly, measurement of a plurality of the measurement items can be carried out simultaneously and quickly.

With the sixth biochemical analysis apparatus in accordance with the present invention, the test film accommodating means is constituted to accommodate a plurality of the test films, the sample application means is provided with the sample applying nozzle moveable along a straight line or a circular arc, and the liquid sample take-out position at which the liquid sample is taken up by the sample application means and all of the sample applying positions at which the liquid sample is applied onto a plurality of the test films are disposed on the straight line or the circular arc corresponding to the movement path of the sample applying nozzle. Therefore, the operations of the sample application means are simple, the mechanism of a movement means for moving the sample application means can be simplified, operation failures can be minimized, and the cost of the apparatus can be reduced. Also, the time required for the movement of the sample application means can be shortened, and processing can be carried out quickly.

BRIEF DESCRIPTION OF THE DRAWINGS

FIG. 4 is a graph showing the rates of deterioration of an unused long test film with the passage of time when the unused long test film is maintained under various temperature-humidity conditions, in terms of the number of days for which the long test film can be stored under such conditions without becoming unusable for measurement, FIG. 5 is a sectional view taken along line 5—5 of FIG. 3, FIG. 11 is a plan view showing a further embodiment of the biochemical analysis apparatus in accordance with the present invention.

DESCRIPTION OF THE PREFERRED EMBODIMENTS

The present invention will hereinbelow be described in further detail with reference to the accompanying drawings.

Figure 1:
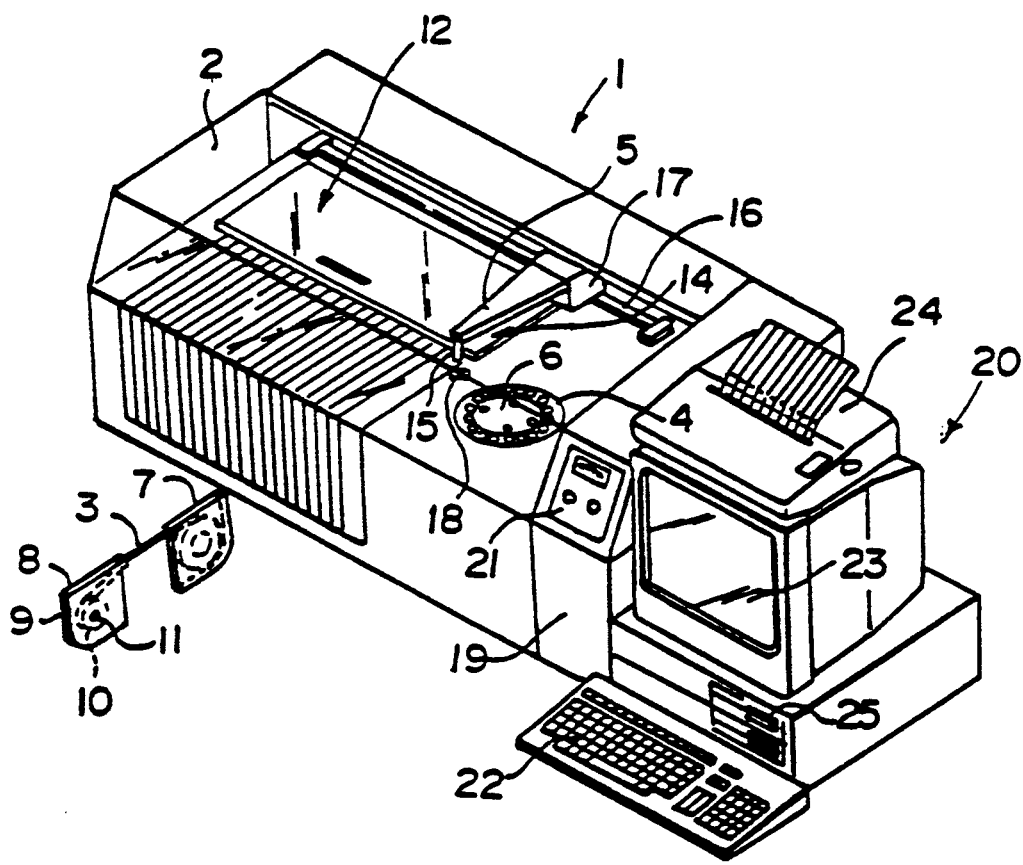
FIG. 1 is a perspective view showing an embodiment of the biochemical analysis apparatus in accordance with the present invention.

With reference to FIG. 1, a biochemical analysis apparatus 1 is provided with a transparent cover 2, and a liquid sample, a long tape-like test film 3 and the like are fed into and out of the apparatus 1 by opening the cover 2. The apparatus 1 is provided with a sample accommodating means 4 for accommodating a liquid sample such as blood serum or urine along a ring-like area, and the liquid sample is taken up from the sample accommodating means 4 and applied by a sample application means 5 as will be described later. A centrifugation means 6 is provided inward from the sample accommodating means 4 for accommodating body fluid, for example, blood (whole blood), and centrifuging the blood to produce blood serum as the liquid sample, and for other purposes. The long test film 3 contains a reagent undergoing a color reaction with only a specific chemical constituent or a specific physical constituent that is to be analyzed in the liquid sample, and many kinds of the long test films are prepared in accordance with the measurement items. An unused portion of the long test film 3 which has not yet been used for measurement is wound up in a film feed cassette 7, and the used portion of the long test film 3 which has already been used for measurement is wound up in a film wind-up cassette 8. The lot number, film number, measurement item, working life and other information on the long test film 3 are indicated by, for example, a bar code 9, on one face of the film wind-up cassette 8. At the center of a reel 10 in the film wind-up cassette 8, a hole 11 is provided for engagement with a rotation shaft of a motor for pulling the long test film 3 out of the film feed cassette 7 after the long test film 3 has been accommodated in the biochemical analysis apparatus 1 as will be described later. The long test film 3 is accommodated in the biochemical analysis apparatus 1 in the form wound up in the film feed cassette 7 and the film wind-up cassette 8. As shown in FIG. 1, the film feed cassette 7 and the film wind-up cassette 8 are formed independently of each other. A test film accommodating means 12 accommodates unused portions of a plurality of the long test films 3 in parallel so that various items of measurements can be carried out simultaneously by use of the apparatus 1. At the right end of the test film accommodating means 12 in FIG. 1, an electrolyte determination slide accommodating region 14 is provided for accommodating electrolyte determination slides for determination of electrolytes such as $Na^+$, $K^+$ and $Cl^-$ in the liquid sample. The unused slides are stacked in the accommodating region 14. The sample application means 5 is provided with a sample applying nozzle 15 at the end, and is moved in the extending direction of a rail 16 by a movement means 17 placed on the rail 16 for taking up the liquid sample from the sample accommodating means 4 or the centrifugation means 6, and applying the liquid sample onto the long test film 3 pulled out by a test film conveyance means from the test film accommodating means 12 or onto the electrolyte determination slide pushed out of the electrolyte determination slide accommodating region 14. The movement means 17 also moves the sample application means 5 vertically. The sample application means 5 is kept at its upper position at the time it is moved by the movement means 17 in the extending direction of the rail 16, and is moved down at the time of taking out and application of the liquid sample and at the time of washing as will be described later.

In this specification, both the electrolyte determination slide and the long test film 3 are generically referred to as the test film.

After applying the liquid sample onto the test film, the sample applying nozzle 15 is washed at a nozzle washing region 18 provided close to the electrolyte determination slide accommodating region 14 and the sample accommodating means 4 therebetween in accordance with the operation sequence as will be described later, and is reused for sample application.

The test film on which the liquid sample has already been applied is incubated by an incubator as will be described later, and subjected to measurement by a measurement means.

Control of operations of the overall apparatus 1, processing of the measurement data and the like are carried out by a circuit region 19 and a computer 20 connected therewith. An operating and display region 21 on the front surface of the circuit region 19 is provided with a power source switch for the apparatus 1, an ammeter for monitoring the current consumption in the apparatus 1, and other members. The computer 20 is provided with a keyboard 22 for giving instructions to the apparatus 1, a CRT display device 23 for displaying the subsidiary information for instructions, measurement results and other items, a printer 24 for printing the measurement results, and a floppy disk drive unit 25 for accommodating a floppy disk for storage of commands for giving various instructions to the apparatus 1 and the information on the measurement results.

Figure 2:
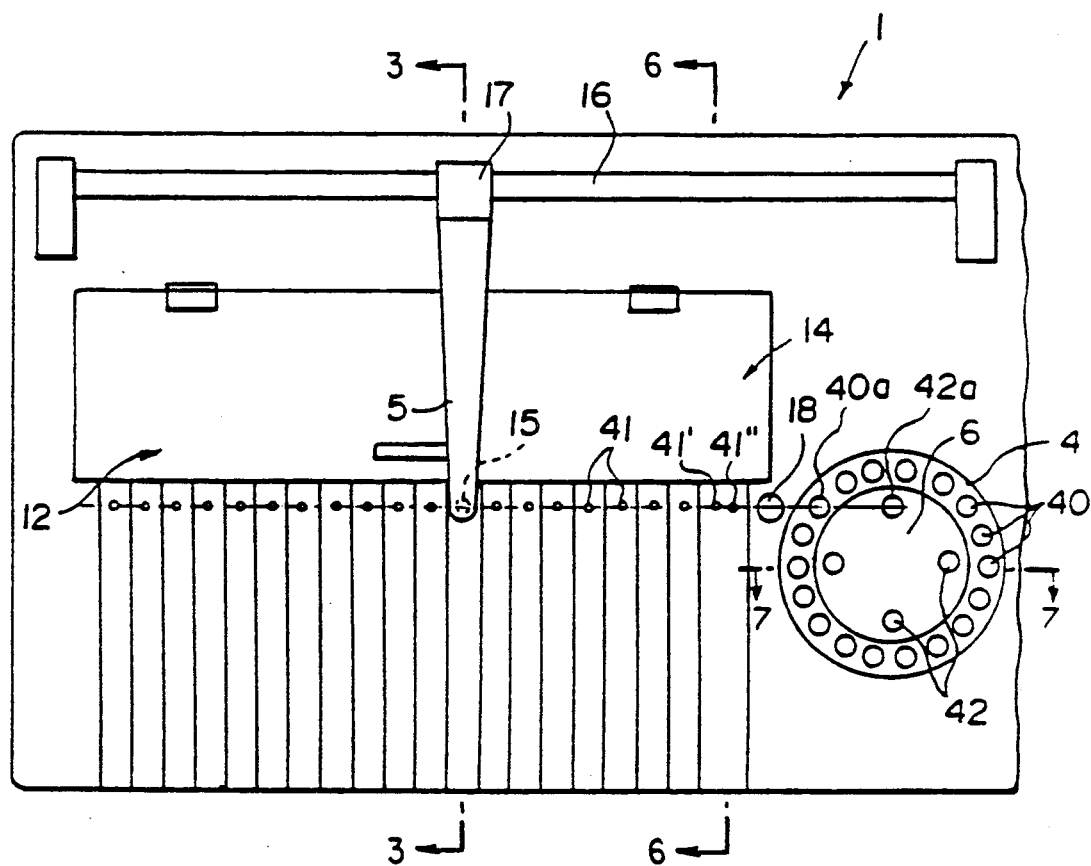
FIG. 2 is a plan view showing the major part of the embodiment shown in FIG. 1.

With reference to FIG. 2 showing the major part of the apparatus 1, the test film accommodating means 12 is constituted so that sample applying positions 41 41' and 41" for all of the test films pulled out or pushed out of the test film accommodating means 12 stand in a straight line indicated by the chain line. Also, the nozzle washing region 18, a liquid sample take-out position 40a in the sample accommodating means 4, and a liquid sample take-out position 42a in the centrifugation means 6 are disposed on said straight line. The arrangement on the straight line simplifies the configuration of the movement means as will be described later, which in turn contributes to a decrease in operation failures and cost of the apparatus 1.

The sample accommodating means 4 accommodates a plurality of liquid samples in accommodating regions 40 disposed in the ring-like area. The accommodating regions 40 are automatically rotated along the circular path until the liquid sample which is accommodated in one of the accommodating regions 40 and which is to be used for the next measurement arrives at the take-out position 40a. In order to prevent the liquid samples accommodated in the accommodating regions 40 from evaporating and deteriorating, a cover (not shown) is provided on the accommodating regions 40 outside of the take-out position 40a.

The centrifugation means 6 accommodates body fluid in accommodating regions 42 and centrifuges it. Thereafter, as in the case of the sample accommodating means 4, the accommodating regions 42 are rotated until the liquid sample is located at the take-out position 42a in the sequence of take-out by the sample application means 5. By way of example, the body fluid is blood (whole blood). Upon centrifugation of the whole blood, blood plasma is separated up, and blood clot sediments. In this case, blood serum or blood plasma as the liquid sample can be taken up by the sample application means 5 without being separated into a vessel different from the vessel of blood clot. As in the case of the sample accommodating means 4, a cover (not shown) is provided on the accommodating regions 42 of the centrifugation means 6.

The sample application means 5 is moved by the movement means 17 in the extending direction of the rail 16, takes up the liquid sample from the take-out position 40a or the take-out position 42a, and applies it to the sample applying position 41 or 41' on the test film. Both the liquid sample and a reference solution should be applied to the electrolyte determination slide, and therefore the sample applying positions 41' and 41" are provided. The liquid sample is applied to the sample applying position 41', and the reference solution is applied to the sample applying position 41".

Figure 3:
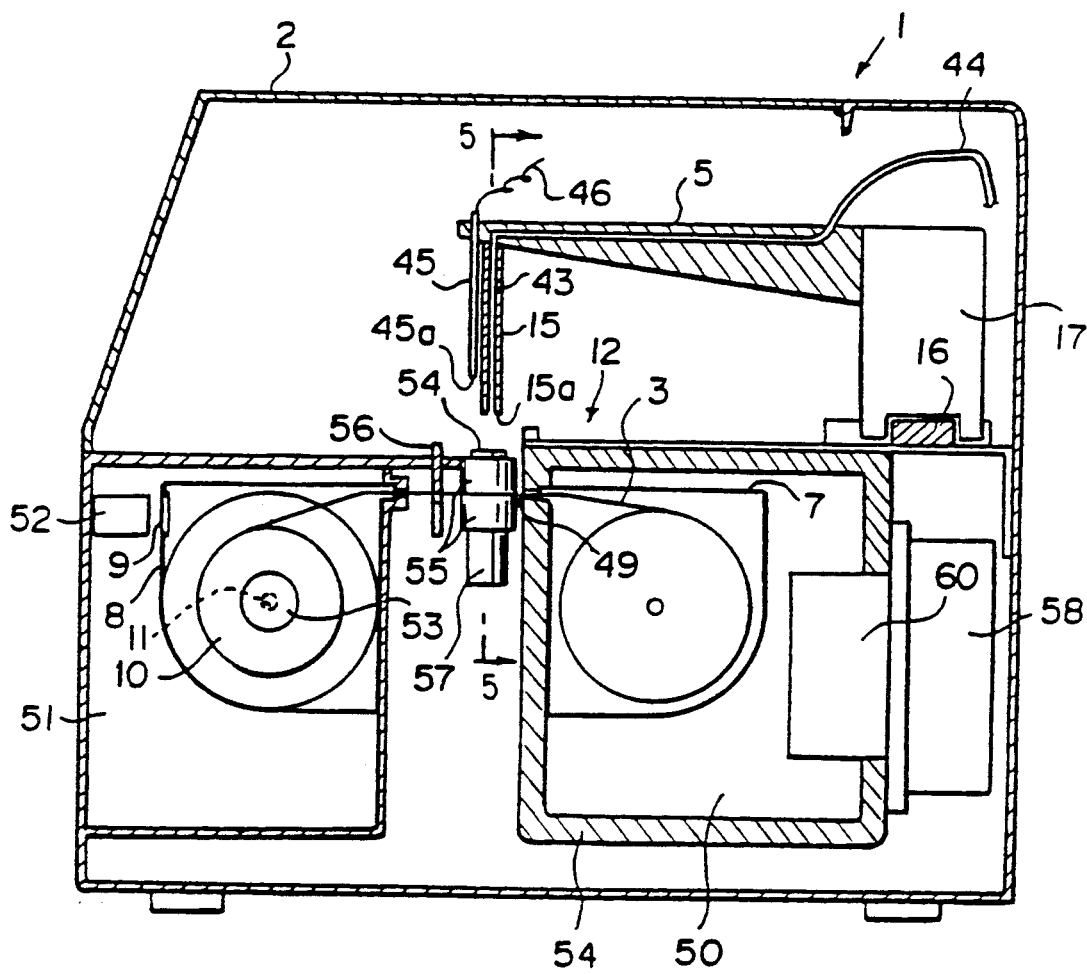
FIG. 3 is a sectional view taken along line 3—3 of FIG. 2.

FIG. 3 is a sectional view taken along line 3—3 of FIG. 2. In FIG. 3, similar elements are numbered with the same reference numerals with respect to FIGS. 1 and 2. With reference to FIG. 3, the long test film 3 is accommodated in the film feed cassette 7 and the film wind-up cassette 8 and is accommodated in this form in the apparatus 1. The film feed cassette 7 is accommodated in a refrigerator 50 which constitutes the test film accommodating means 12, and the film wind-up cassette 8 is accommodated in a wind-up chamber 51.

With the configuration wherein the unused portion of the long test film 3 is accommodated in the film feed cassette 7, the unused long test film 3 can be accommodated in the test film accommodating means 12 without the hands of the operator contacting the unused long test film 3.

As mentioned above, by way of example, the bar code 9 indicating the lot number, film number, measurement item, working life and other information on the long test film 3 is provided on one face of the film wind-up cassette 8. The information indicated by the bar code 9 is read by a bar code reading means 52 provided at a position in the wind-up chamber 51 corresponding to the position at which the bar code 9 is located when the film wind-up cassette 8 is accommodated in the wind-up chamber 51. The information thus read is stored on, for example, the floppy disk in the floppy disk drive unit 25 shown in FIG. 1, and is used for control of the measurement item and control of the length of the unused film portion remaining in the film feed cassette 7, and elimination of measurement errors caused by fluctuations among production lots of the long test films 3. Also, in the case where the long test film 3 is taken out of the apparatus 1 after being used partially, the film number, the length of the remaining unused film portion and other information on the long test film 3 are stored on the floppy disk unless a deletion command is entered from the keyboard 22 shown in FIG. 1 or until the information is deleted automatically at the time the long test film 3 runs out of the working life. When the long test film 3 is again accommodated in the test film accommodating means 12 for reuse, the film number of the long test film 3 is compared with the information stored on the floppy disk, and the length of the remaining unused portion of the long test film 3 and other items are controlled again.

The aforesaid bar code 9 may be provided on the film feed cassette 7, and the bar code reading means 52 may be provided inside of the refrigerator 50. Also, the means for transmitting the lot number, the working life and other information on the long test film 3 to the apparatus 1 is not limited to the bar code 9 and the means for reading the bar code 9, and any other known means for recording the information on the film feed cassette 7 or on the film wind-up cassette 8 and reading the information at the time the long test film 3 is accommodated in the apparatus 1 may be employed for this purpose.

The refrigerator 50 is enclosed by a refrigerator wall 54 composed of a heat insulating material. A cooling and dehumidifying device 58 for keeping the inside of the refrigerator 50 at a predetermined low temperature and low humidity is provided on one surface of the refrigerator wall 54, and air inside of the refrigerator 50 is circulated by a fan 60.

FIG. 4 shows the rates of deterioration of the unused long test film 3 with the passage of time when the unused long test film 3 is maintained under various temperature-humidity conditions, in terms of the number of days for which the long test film 3 can be stored under such conditions without becoming unusable for measurement. Each of the numerals indicated in the circles in FIG. 4 represents the number of days for which the long test film 3 can be stored under the temperature-humidity conditions corresponding to the circle without becoming unusable for measurement. The number of days for which the long test film 3 can be stored under the temperature-humidity conditions without becoming unusable for measurement increases sharply at the left bottom of the graph (under a low temperature, low humidity conditions) shown in FIG. 4. Therefore, the long test film 3 can be stored for a longer period in the apparatus 1 by accommodating the unused portion of the long test film 3 in the refrigerator 50 and maintaining the unused portion at a predetermined low temperature and low humidity adjusted by considering the working life and the working frequency of the long test film 3 and other items.

Reverting to FIG. 3, when the film wind-up cassette 8 is accommodated in the wind-up chamber 51, a rotation shaft of a test film wind-up motor 53 constituting the test film conveyance means for the long test film 3 provided in the wind-up chamber 51 engages with a hole 11 formed at the center of a reel 10 of the film wind-up cassette 8. As the motor 53 is rotated, the long test film 3 is pulled out of the film feed cassette 7 through a film outlet 49 of the refrigerator 50, and is wound up in the film wind-up cassette 8. As mentioned above, the film feed cassette 7 and the film wind-up cassette 8 are provided independently of each other. Therefore, the film outlet 49 of the refrigerator 50 may be as small as to allow the passage of the long test film 3 therethrough, and the cooling and dehumidifying efficiency in the refrigerator 50 can be maintained high. Also, the long test film 3 can also be used in various apparatuses among which the distance between the refrigerator 50 and the wind-up chamber 51 differs. Furthermore, with the configuration wherein the used portion of the long test film 3 is accommodated in the film wind-up cassette 8, the used long test film 3 on which the liquid sample has already been applied can be taken out of the apparatus 1 and discarded or processed for other purposes without the hands of the operator contacting the used long test film 3. For discarding the used long test film 3, a cutter for cutting the used film may be provided near the inlet of the wind-up chamber 51, and a box for receiving the cut film fragments and capable of being fitted to and removed from the apparatus 1 may be provided instead of the wind-up chamber 51. With this configuration, the used film contained in the box can be taken out of the apparatus 1 together with the box and discarded or processed for other purposes without the hands of the operator contacting the used film. In this case, conveyance of the test film may be carried out by the provision of conveying rollers for grasping and conveying the test film.

The exposed portion of the long test film 3 between the film feed cassette 7 and the film wind-up cassette 8 passes through an incubator 55 provided with a shutter 54 and between a light projector and a light receiver of a photoelectric switch 56. A measuring device 57 for measuring the optical density produced by a color reaction of the long test film 3 with the liquid sample is disposed under the incubator 55.

With the configuration illustrated in FIG. 3 wherein the refrigerator 50 and the incubator 55 are close to each other, the length of the portion of the long test film 3 pulled out of the film feed cassette 7 for a single measurement may be short so that more measurements can be achieved with the long test film 3 of the same length.

With reference to FIG. 5 illustrating the configuration of the incubator 55 along line 5—5' of FIG. 3, the long test film 3 is pulled out of the film feed cassette 7 and intermittently moved from the rear of the drawing sheet in FIG. 5 to the front thereof. Prior to this step, an upper cover 55a of the incubator 55 has been moved in the direction as indicated by the arrow A. After the long test film 3 has been moved as mentioned above, the upper cover 55a is moved in the direction as indicated by the arrow B, and pushes down the long test film 3 as illustrated. Then, the shutter 54 is moved in the direction as indicated by the arrow C, the sample application means 5 is moved down to apply the liquid sample from the sample applying nozzle 15 onto the long test film 3 through a hole 59. Thereafter, the shutter 54 is moved in the direction as indicated by the arrow D to close the hole 59 as illustrated and prevent air flow between the inside and outside of the hole 59, and the incubator 55 incubates so that the temperature in the inside thereof reaches a predetermined value, for example, 37° C. In the course of the incubation or after the incubation is finished, the optical density at the portion of the long test film 3 on which the liquid sample has already been applied is measured by the measuring device 57. Instead of providing the shutter 54, the upper cover 55a of the incubator 55 may be constituted moveable in the directions as indicated by the arrows C and D as well as in the directions as indicated by the arrows A and B. In this case, the upper cover 55a of the incubator 55 need not be provided with the hole 59 for sample application. But instead, after the liquid sample has been applied onto the long test film 3 by moving the upper cover 55a in the direction as indicated by the arrow C, the upper cover 55a may be moved to its original position in the direction as indicated by the arrow D, and incubation may then be carried out.

With this embodiment wherein the sample application, incubation and measurement are carried out at a single position, the position to which the liquid sample has been applied is incubated and measured reliably even though the accuracy of feed of the long test film 3 by the test film wind-up motor 53 is low. Also, since the sample applying position 41 (as shown in FIG. 2) with respect to the incubator 55 is always constant, the temperature distribution inside of the incubator 55 is constant, the color reaction is effected under constant conditions, and the measurement accuracy becomes high. Furthermore, in the case where the sample application, incubation and measurement are carried out at different positions, it is necessary for the rotation of the motor 53 to be controlled each time the long test film 3 is to be moved from the sample applying position to the incubating position or from the incubating position to the measuring position. However, with the aforesaid embodiment wherein the sample application, incubation and measurement are carried out at a single position, such complicated control is not required.

The photoelectric switch 56 shown in FIG. 3 detects holes or marks of the long test film 3. Based on the signal generated by the photoelectric switch 56, the long test film 3 is pulled out of the film feed cassette 7 by a length necessary for a single measurement. The computer 20 shown in FIG. 1 counts the number of pull-out operations of the long test film 3, and issues a warning, for example, by sound or light, to the operator when the length of the remaining unused portion of the long test film 3 has decreased to a predetermined value or less. Also, a hole or a mark discriminable by the photoelectric switch 56 from the holes or marks provided at the predetermined measurement length intervals on the long test film 3 is provided near the tail edge portion of the long test film 3. When the hole or mark near the tail edge portion of the long test film 3 is detected, the photoelectric switch 56 produces a signal for stopping the pull-out of the long test film 3. The end of the long test film 3 may be judged on the basis of only the value counted by the computer 20. However, the end mark or the like should preferably be provided on the long test film 3 itself to cope with the case wherein the long test film 3 is taken out of the apparatus 1 after it has partially been used for measurement, and is artificially wound up slightly and then loaded to the apparatus 1 again.

An elongated pipe 43 continuing into a leading end 15a of the sample applying nozzle 15 is provided in the sample application means 5. The pipe 43 is communicated with a flexible pipe 44 so that the liquid sample is fed through the pipes 43 and 44 into the sample application means 5 and applied onto the test film as will be described later. The reference solution is fed and washing liquid is delivered through the pipes 43 and 44.

A liquid level detector 45 is provided in parallel with the sample applying nozzle 15 in the vicinity thereof. The liquid level detector 45 is provided so that its leading edge 45a is slightly (for example, by approximately 2.5 mm) higher than the leading edge 15a of the sample applying nozzle 15. When the sample application means 5 is moved down by the movement means 17 for taking up the liquid sample accommodated in the sample accommodating means 4 or the centrifugation means 6, the leading edge 15a of the sample applying nozzle 15 enters the liquid sample, and the leading edge 45a of the liquid level detector 45 contacts the liquid sample. At this time, a signal indicating that the leading edge 45a of the liquid level detector 45 has contacted the liquid sample is produced by the liquid level detector 45, and transmitted to the circuit region 19 shown in FIG. 1 through a signal line 46. Based on the signal, the downward movement of the sample application means 5 is stopped. In this manner, the leading edge 15a of the sample applying nozzle 15 can be entered into the liquid sample up to a predetermined depth from the surface of the liquid sample regardless of the amount of the liquid sample.

Figure 6:
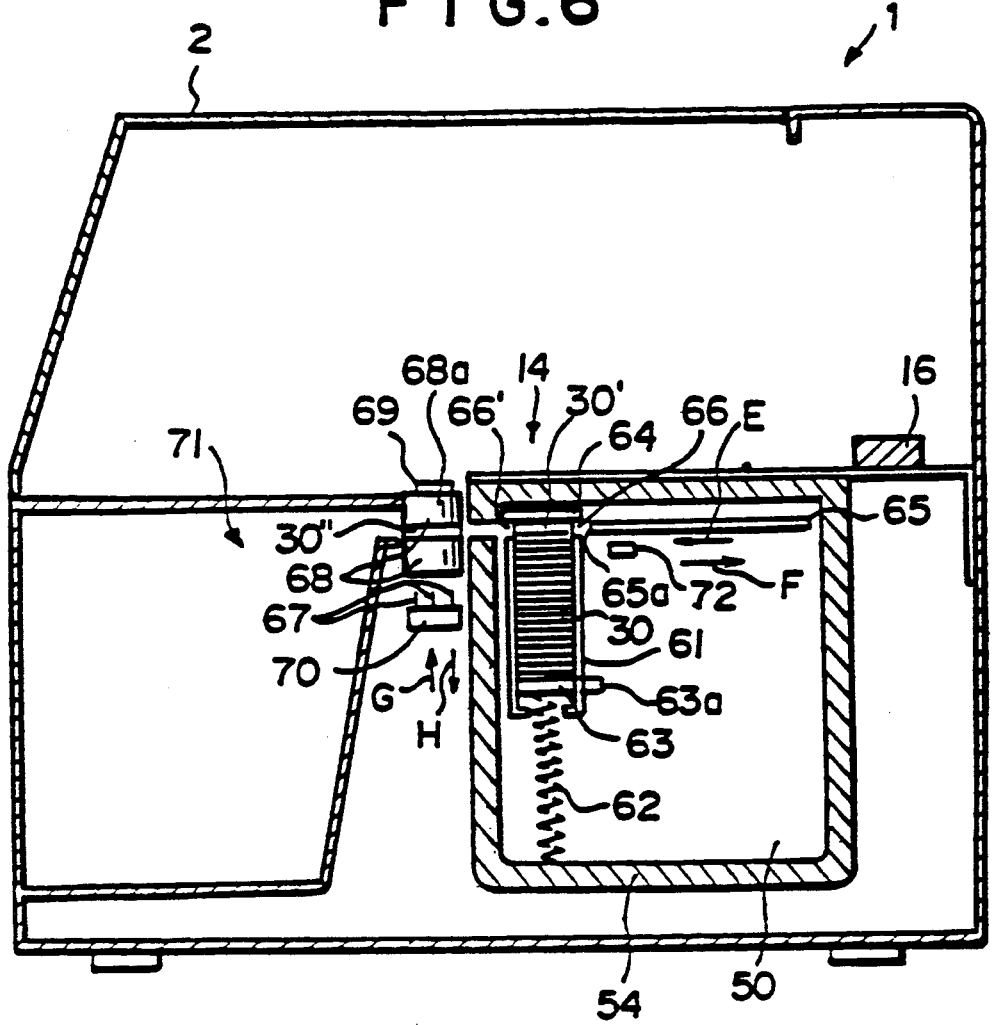
FIG. 6 is a sectional view taken along line 6—6 of FIG. 2.

With reference to FIG. 6 illustrating the configuration of the electrolyte determination slide accommodating region 14 along line 6—6 of FIG. 2, electrolyte determination slides 30 are stacked in a slide magazine 61, and a bottom plate 63 of the slide magazine 61 is urged up by a spring 62. The top slide 30' among the electrolyte determination slides 30 is pushed up against a top plate 64 of the slide magazine 61. A slide conveying member 65 constituting the test film conveyance means for the slides 30 is moveable by a drive means (not shown) in the directions as indicated by the arrows E and F. As the slide conveying member 65 is moved in the direction as indicated by the arrow E, a leading edge 65a thereof enters a slit 66 formed in the slide magazine 61, and pushes the top slide 30' in the slide magazine 61. As a result, the slide 30' is pushed out of the slide magazine 61 through a slit 66' into an incubator 68 as indicated by a reference numeral 30''. At the incubator 68, a shutter 69 is opened, a sample liquid is applied to the slide 30'', the shutter 69 is then closed, and the slide 30'' is incubated. Thereafter, a measuring device 70 is moved up in the direction as indicated by the arrow G until potential measuring probes 67 contact electrodes (not shown) of the slide 30'' in the incubator 68, and a difference in potential is measured. Thereafter, the measuring device 70 is moved in the direction as indicated by the arrow H to its waiting position as shown in FIG. 6. The incubator 68 has nearly the same configuration as the incubator 55 for the long test film 3 shown in FIG. 5, except that the slide 30' pushed out by the slide conveying member 65 can be accommodated as the slide 30'', and the liquid sample and the reference solution can be applied to the predetermined positions on the slide 30''. Also, instead of providing the measuring device 57 shown in FIG. 5, the probes 67 of the measuring device 70 moved in the direction as indicated by the arrow G in FIG. 6 contact the predetermined electrodes to measure a difference in potential.

As in the case of the long test film 3, instead of providing the shutter 69, the effect of the shutter 69 may be achieved by an upper cover 68a of the incubator 68. Also, since the sample application, incubation and measurement are carried out at a single position, the same effects as in the case of the long test film 3, such as simplification of the control of push-out of the slide 30' by the slide conveying member 65 and improved measurement accuracy, can be obtained.

After the measurement is finished, the slide 30'' is pushed by the slide conveying member 65 leftward in FIG. 6 into a slide discarding region 71. The slide conveying member 65 is then moved in the direction as indicated by the arrow F to the waiting position shown in FIG. 6.

As the slides 30 are pushed one by one out of the slide magazine 61, the bottom plate 63 of the slide magazine 61 is pushed up by the spring 62. At the time a protrusion 63a projecting from the bottom plate 63 out of the slide magazine 61 faces a proximity switch 72, a warning is issued to the operator to instruct replenishment of slides 30. In the case where a predetermined number of the slides 30 are then pushed out of the slide magazine without new slides replenished and the slide magazine 61 runs out of the slide 30 while the liquid sample to be measured for a difference in potential is still present, the apparatus 1 is stopped without sample application and other operations for measurement of the liquid sample being carried out.

Figure 7:
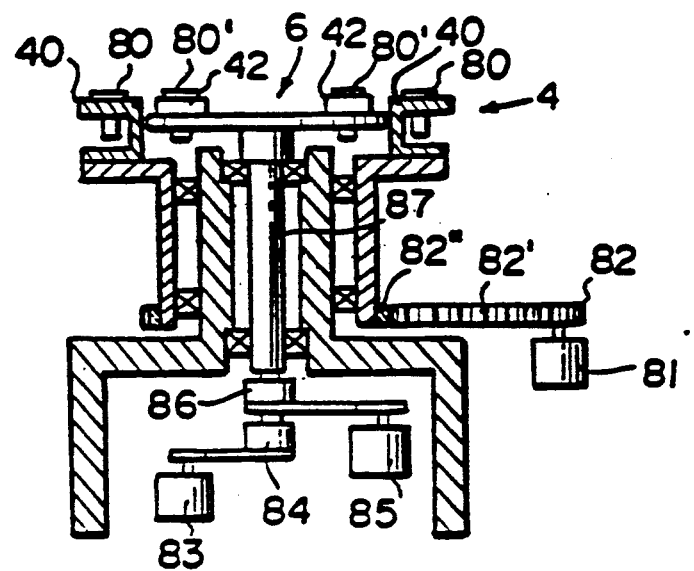
FIG. 7 is a sectional view taken along line 7—7, of FIG. 2.

With reference to FIG. 7 illustrating the sample accommodating means 4 and the centrifugation means 6 along line 7—7 of FIG. 2, the sample accommodating means 4 is constituted so that sample cups 80 for containing the liquid samples are placed in the accommodating regions 40 provided in the ring-like area on the upper surface of the sample accommodating means 4, and the overall sample accommodating means 4 is rotated by a motor 81 via gears 82, 82' and 82''. The operation of the motor 81 is controlled so that the liquid samples are located one after another at the liquid sample take-out position 40a shown in FIG. 2 in the sequence of take-out from the sample accommodating means 4 and sample application.

Sample cups 80' containing body fluid are placed in the accommodating regions 42 on the upper surface of the centrifugation means 6. From the viewpoint of cup control and reduction in cost, cups of the same type as the sample cups 80 on the sample accommodating means 4 are employed as the sample cup 80'.

A motor 83 is provided for centrifugation. A motor 85 rotates the sample cups 80', to locate the liquid sample (body fluid) after centrifugation at the liquid sample take-out position 42a shown in FIG. 2 as in the case of the motor 81.

At the time centrifugation is to be carried out, a clutch 86 is disengaged to disconnect the motor 85 from a rotation shaft 87, and a clutch is engaged to transmit the power of the motor 83 to the rotation shaft 87. The motor is operated in this condition to rotate the sample cups 80' at a high speed with the bottoms of the sample cups 80' facing outward and openings thereof facing inward by the centrifugal force so that the body fluid does not spill out of the sample cups 80', 80', . . . After centrifugation is thus carried out for a predetermined time, the clutch 84 is disengaged to disconnect the motor 83 from the rotation shaft 87, and the clutch 86 is engaged to connect the motor 85 to the rotation shaft 87. The motor 85 is then operated to rotate the sample cups 80' until the liquid sample (body fluid) after centrifugation is located at the liquid sample take-out position 42a shown in FIG. 2.

As the centrifugation means 6 is provided in the space inward from the sample accommodating means 4, the overall apparatus 1 can be made small. Also, since the accommodating regions 42 of the centrifugation means 6 are provided inward from the accommodating regions 40 arranged in the ring-like area of the sample accommodating means 4, feed of the liquid sample (body fluid) to the apparatus 1 for measurement can be carried out at a single position, and therefore a high operating efficiency can be obtained.

Figure 8:
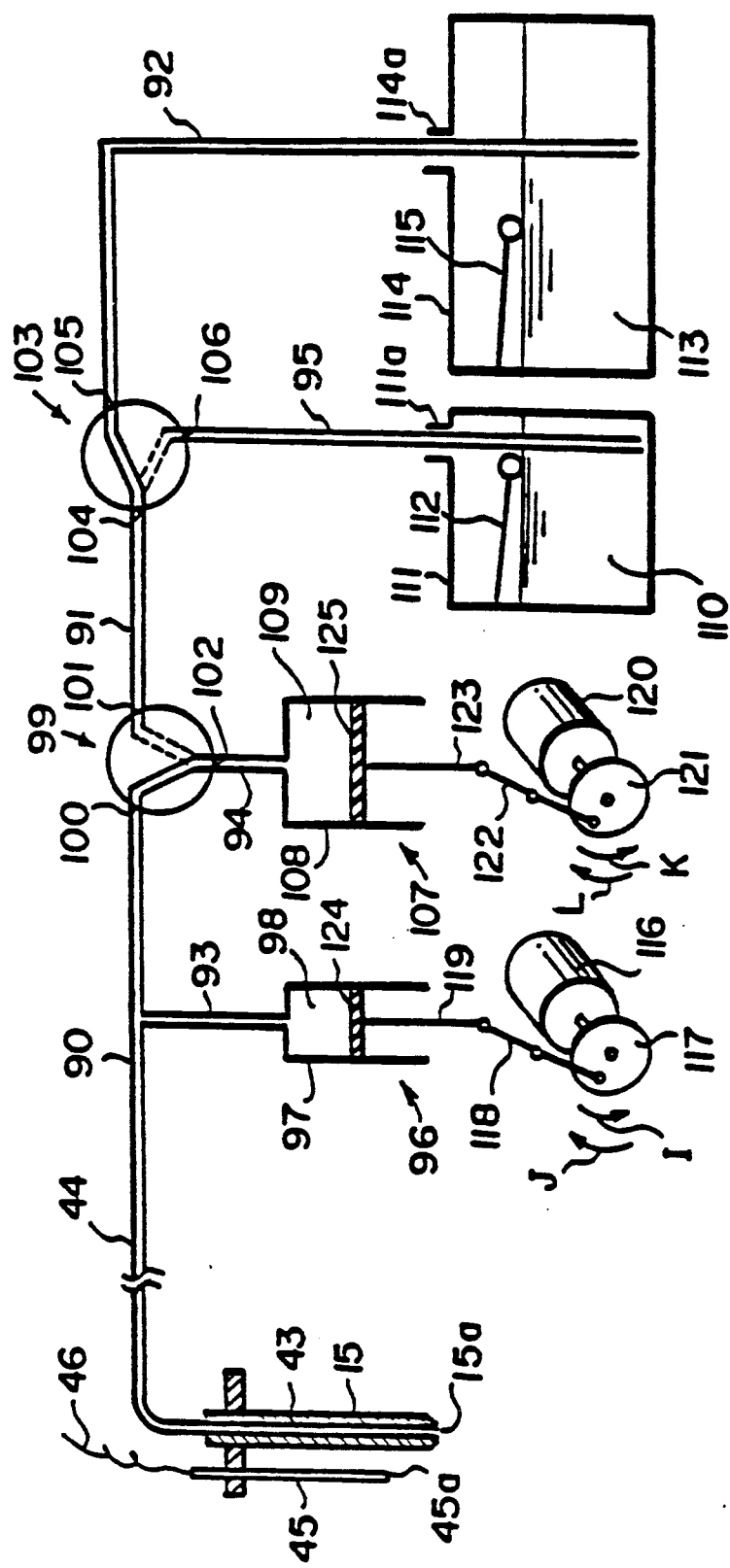
FIG. 8 is a flow diagram showing the pipes communicating with a pipe of a sample application nozzle.

With reference to FIG. 8 showing the pipes communicating with the pipe 43 passing through the center of the sample applying nozzle 15 of the sample application means 5, the pipe 43 communicates with the flexible pipe 44 which communicates with an end of a pipe 90. The pipe 90 communicates at its intermediate point with a pipe 93 communicating with a space 98 in a cylinder 97 of a suction and delivery means 96, and the other end of the pipe 90 is connected to a port 100 of a solenoid valve 99. A pipe 91 connects a port 101 of the solenoid valve 99 with a port 104 of a solenoid valve 103. A port 102 of the solenoid valve 99 is connected to a pipe 94 communicating with a space 109 in a cylinder 108 of a suction and delivery means 107. The solenoid valve 99 is changed over by a signal received from the exterior to communicate the pipes 90 and 94 with each other and disconnect the pipe 91 from the pipe 94, or conversely to communicate the pipes 91 and 94 with each other and disconnect the pipe 90 from the pipe 94. A port 106 of the solenoid valve 103 is connected to an end of a pipe 95 having the other end extending to the vicinity of the bottom of a tank 111 via an opening 111a of the tank 111 and immersed in a reference solution 110 in the tank 111. A liquid level detector 112 is provided in the tank 111 for detecting the level of the reference solution 110 in the tank 111. A signal indicating the level of the reference solution 110 is transmitted to the circuit region 19 shown in FIG. 1 via a signal line (not shown), and a warning is issued by, for example, sound or light, to the operator when the level of the reference solution 110 is low. A port 105 of the solenoid valve 103 is connected to an end of a pipe 92 having the other end extending to the vicinity of the bottom of a tank 114 via an opening 114a of the tank 114 and immersed in a washing liquid 113 in the tank 114. As in the case of the tank 111, a liquid level detector 115 is provided in the tank 114. The solenoid valve 103 is changed over by a signal received from the exterior to communicate the pipes 91 and 92 with each other and disconnect the pipe 91 from the pipe 95, or conversely to communicate the pipes 91 and 95 with each other and disconnect the pipe 91 from the pipe 92.

The suction and delivery means 96 sucks the liquid sample from the leading edge 15a of the sample applying nozzle 15, and applies it therefrom onto the test film. In order to suck the liquid sample, the leading edge 15a of the sample applying nozzle 15 is entered into the liquid sample accommodated in the sample accommodating means 4 or the centrifugation means 6 until the leading edge 45a of the liquid level detector 45 contacts the surface of the liquid sample, and the solenoid valve 99 is controlled so that the pipes 90 and 94 disconnect from each other and the pipes 91 and 94 communicate with each other. In this condition, the motor 116 is rotated in the direction as indicated by the arrow I, the rotation force is converted into linear motion via a cam plate 117 and a link mechanism 118, and the linear motion is transmitted to a piston rod 119. As a result, the piston rod 119 is moved down to pull a piston 124 down and broaden a space 98 inside of the cylinder 97. In this manner, the liquid sample is moved from the leading edge 15a of the sample applying nozzle 15 to the pipes 43, 44 and 90. The sample application means 5 is constituted to be capable of accommodating the liquid sample, at one time, in an amount necessary for achieving the sample application sequentially to a plurality of the long test films, which contain the reagents different in accordance with the measurement items and which are accommodated in the test film accommodating means 12. In order to apply the liquid sample onto the test film, the sample application means 5 is moved to the sample applying position of the test film, the shutter 54 or the shutter 69 is opened, the sample applying nozzle 15 is moved down, and then the motor 116 is rotated in the direction as indicated by the arrow J. As a result, the drive force of the motor 116 is transmitted to the piston rod 119 via the cam plate 117 and the link mechanism 118, the piston rod 119 is moved up to push the piston 124 up, and the liquid sample is applied in an amount corresponding to the extent of the movement of the piston 124.

In order to deliver the reference solution 110 from the leading edge 15a of the sample applying nozzle 15, the solenoid valve 99 is first controlled so that the pipes 91 and 94 communicate with each other and the pipes 90 and 94 are disconnected from each other, and the solenoid valve 103 is controlled so that the pipes 91 and 95 communicate with each other and the pipes 91 and 92 are disconnected from each other. In this condition, the motor 120 is rotated in the direction as indicated by the arrow K, the rotation force is converted into linear motion via a cam plate 121 and a link mechanism 122, and the linear motion is transmitted to a piston rod 123. As a result, the piston rod 123 is moved down to pull a piston 125 down and broaden a space 109 inside of the cylinder 108. In this manner, the reference solution 110 is moved through the pipe 95, the solenoid valve 103, the pipe 91, the solenoid valve 99 and the pipe 94 into the space 109 in the cylinder 108. Then, the solenoid valve 99 is controlled so that the pipes 90 and 94 communicate with each other and the pipes 91 and 94 are disconnected from each other. Thereafter, the motor 120 is rotated in the direction as indicated by the arrow L to move the piston rod 123 up and push the piston 125 up, and the reference solution 110 is delivered from the leading edge 15a of the sample applying nozzle 15 in an amount corresponding to the extent of movement of the piston 125.

Delivery of the washing liquid 113 from the leading edge 15a of the sample applying nozzle 15 is controlled in the same manner as the delivery of the reference solution 110, except that the solenoid valve 103 is controlled so that the pipes 91 and 92 communicate with each other and the pipes 91 and 95 are disconnected from each other when the washing liquid 113 is to be moved to the space 109 in the cylinder 108.

With the aforesaid pipe connections, the sample applying nozzle 15 works for both the liquid sample and the reference solution, and it is not necessary to use dual nozzles as disclosed in, for example, Japanese Unexamined Patent Publication No. 61(1986)-173131. With this embodiment wherein a single nozzle is used, the mechanism is simplified, operation failures decrease, and the cost decreases.

Also, with the aforesaid embodiment wherein the opening 111a of the tank 111 containing the reference solution 110 is made as small as to allow insertion of the pipe 95 thereinto, evaporation and deterioration of the reference solution 110 can be prevented as compared with the case where the reference solution 110 is kept to stand in the sample cups 80 at the accommodating regions 40 as in the case of the liquid sample. Furthermore, with the substantially large tank 111, no replenishment of the reference solution 110 thereto is required for a long period.

Operations of the embodiment the biochemical analysis apparatus in accordance with the present invention shown in FIG. 1 will be described hereinbelow. It is ordinarily practiced that a monitor means for monitoring the operating condition is provided on the apparatus 1, thereby automatically carrying out processing such as stop of the apparatus 1 and issuance of a warning to the operator in the case of abnormal operation. Therefore, processing in the case of abnormal operation will be only briefly described below.

First, the power source switch of the apparatus 1 is turned on by the operator to supply electric power to the apparatus 1 only after the necessary test film has been accommodated in the apparatus 1. In the case where the power switch is off and the test film is present in the test film accommodating means 12, the cooling and dehumidifying device 58 is kept energized to maintain the inside of the refrigerator 50 at a predetermined temperature and humidity.

After the electric power is supplied to the apparatus 1, initial setting of the apparatus 1 is carried out in the sequence described below. Specifically, in the case where the sample application means 5 is not at its upper position, it is moved to its upper position by the movement means 17. The sample application means 5 is then moved by the movement means 17 to a predetermined end of the rail 16.

Thereafter, the sample application means 5 is moved by the movement means 17 toward the washing region 18, and is stopped by a signal received from a position detection means (not shown) for producing the signal at the time the sample application means 5 arrives at the washing region 18. On the other hand, by way of example, a pulse encoder (not shown) is provided on a shaft of a motor (not shown) for moving the sample application means 5 along the rail 16. The pulses produced by the pulse encoder in proportion to the amount of rotation of the motor are counted during the movement of the sample application means 5 from the predetermined end of the rail 16 to the washing region 18. Based on the number of the pulses counted, the presence or absence of slipping between the shaft of the motor and the movement of the sample application means 5 along the rail 16 is detected.

The positions of the pistons 124 and 125 shown in FIG. 8 are monitored to detect whether they are or are not at their start positions that make the space 98 and the space 109 smallest. In the case where the pistons 124 and 125 are not at their start positions, the motors 116 and 120 are rotated in the directions as indicated by the arrows J and L, respectively, to move the pistons 124 and 125 to their start positions. At this time, the solenoid valve 99 is controlled so that the pipes 90 and 94 communicate with each other. In the case where there has been liquid remaining in, for example, the space 109 in the cylinder 108, the liquid is delivered from the leading edge 15a of the sample applying nozzle 15 to the washing region 18 via the pipe 43.

The shutter 54 shown in FIG. 3 and the shutter 69 shown in FIG. 6 are monitored to detect whether they are present at the positions closing the incubators 55 and 68, and the inside of the incubator 55 and the inside of the incubator 68 are maintained at the predetermined temperature.

Also, monitor is effected to detect whether, for example, the levels of the reference solution 110 and the washing liquid 113 in the tanks 111 and 114 are or are not higher than the predetermined levels, and whether the measuring device 70 and the slide conveyance means 65 are or are not at their waiting positions. Then, issuance of a warning to the operator when necessary and automatic shifting to the initial condition are carried out.

After the apparatus 1 has been set to the initial condition in the manner described above, the completion of the initial setting is indicated to the operator.

Thereafter, the operator pours the liquid sample which need not be centrifuged into the sample cup 80 and places it at a predetermined position in the sample accommodating means 4. Body fluid requiring centrifugation is poured into the sample cup 80', and the sample cup 80' is placed at a predetermined position in the centrifugation means 6. The information on the measuring item for the liquid sample (body fluid) is entered from the keyboard 22 or from a floppy disk storing the information inserted into the floppy disk drive unit 25. The apparatus 1 automatically detects whether the test film corresponding to the measuring item thus specified has been or has not been accommodated in the test film accommodating means 12. Also, the position of the liquid sample (body fluid) in the sample accommodating means 4 (centrifugation means 6) is entered to the apparatus 1 from, for example, the keyboard 22. In the case where measurement is to be carried out for a plurality of the liquid samples (body fluids), the aforesaid operations are repeated.

Thereafter, a measurement start instruction is given by the operator to the apparatus 1 by use of, for example, the keyboard 22, and the automatic measuring operations are started.

First, in the case where the body fluid samples have been accommodated at the centrifugation means 6, centrifugation is carried out by the operations of the motors 83, 85 and the clutches 84, 86. After the centrifugation, the body liquid samples (liquid samples) are located one after another at the liquid sample take-out position 42a in the sequence of measurement.

In the case where the liquid samples have been accommodated at the sample accommodating means 4, they are located one after another at the liquid sample take-out position 40a in the sequence of measurement.

Thereafter, the sample application means 5 positioned at the washing region 18 in the initial condition is moved to suck the liquid sample from the sample accommodating means 4 or the centrifugation means 6 into the pipes 43, 44 and 90 by broadening the space 98 in the cylinder 97 while the level of the liquid sample is monitored by means of the liquid level detector 45. In the case where a plurality of measurements are to be carried out, in order to complete suction of the liquid sample by a single operation and shorten the overall measurement time, the liquid sample is sucked in an amount sufficient for all measurements. At this time, the pipes 43, 44 and 90 have often been filled with the washing liquid by the washing operation as will be described later. Therefore, before the liquid sample is thus sucked, air is slightly sucked into the pipe 43 with the leading edge 15a of the sample applying nozzle 15 present in air, and the leading edge 15a of the sample applying nozzle 15 is then entered into the liquid sample. As a result, an air layer intervenes between the washing liquid and the sucked liquid sample so that they do not mix together.

Then, the sample application means 5 is moved up and moved along the rail 16 to the sample applying position on the test film specified in advance. The case where the liquid sample is applied onto the long test film 3 and the case where it is applied onto the slide 30 will hereinbelow be described separately.

First, in the case where the liquid sample is to be applied to the long test film 3, sample application to the long test film 3 is first carried out even though sample application to the slide 30 is necessary, thereby to shorten the overall measurement time. As described above with reference to FIG. 5, sample application to the long test film 3 is carried out by the operations of the shutter 54 and the upper cover 55a of the incubator 55. In order to minimize deterioration of the long test film 3 with the passage of time, the long test film 3 is pulled out of the film feed cassette 7 by the test film conveyance means exactly prior to the sample application.

In the case where the liquid sample is to be applied to a plurality of the long test films 3 in order to minimize the movement of the sample application means 5 and shorten the overall measurement time, the sample application is basically carried out sequentially from the long test film 3 accommodated at an end among the long test films 3 toward the one at the other end. However, in the case where the measurement sequence is specified by the operator when, for example, measurement results of a measurement item are to be investigated urgently, the sample application is carried out in the specified sequence.

After the liquid sample has been applied to the long test film 3, the long test film 3 is incubated, and the optical density at the portion applied with the liquid sample is measured. The measurement results are fed to the computer 20, necessary calculation processing is carried out, and the results of calculation processing are stored and fed out.

Sample application to the slide 30, when necessary, is carried out as described below.

In the case where sample application is to be carried out for both the slide 30 and the long test film 3, sample application to the long test film 3 is first carried out in the manner as mentioned above, and then the sample application means 5 is moved to the sample applying position 41' of the slide 30, and the liquid sample is applied to the slide 30 in the manner as mentioned above. As in the case of the long test film 3, in order to prevent deterioration of the slide 30, conveyance of the slide 30 from the refrigerator 50 to the predetermined position by the slide conveyance member 65 is carried out exactly prior to the sample application to the slide 30. After the liquid sample has been applied to the slide 30, the sample application means 5 is moved to the nozzle washing region 18. A small vessel (not shown) is placed at the nozzle washing region 18. By way of example, distilled water is contained in the vessel and is made to run so that fresh distilled water is always contained in the vessel. After being moved to the nozzle washing region 18, the sample application means 5 is moved down by the movement means 17 until the leading edge 15a of the sample applying nozzle 15 enters the distilled water.

During the movement of the sample application means 5, the reference solution 110 is accumulated in the cylinder 108 shown in FIG. 8 by the above-mentioned operations. After the leading edge 15a of the sample applying nozzle 15 has been entered to the distilled water, the liquid sample remaining in the pipe 43 and other pipes is delivered from the leading edge 15a of the sample applying nozzle 15. In the case where the pipe 90 and other pipes have been filled with the washing liquid, the washing liquid is then delivered. Also, the reference solution 110 which has slightly been mixed with the washing liquid in the pipe 90 and other pipes is delivered. As a result, the reference solution 110 is filled in the pipes up to the leading edge 15a of the sample applying nozzle 15.

The reference solution 110 is then applied to the predetermined position on the slide 30. The reference solution 110 should be applied to the slide 30 as early as possible (for example, within 3 seconds) after the liquid sample has been applied to the slide 30, and therefore the application of the liquid sample to the slide 30 is carried out after the sample application to the necessary long test film 3 has been finished. With this procedure, when sample application is necessary for both the long test film 3 and the slide 30, take-out of the liquid sample from the sample accommodating means 4 or the centrifugation means 6 can be completed by a single operation, and the overall measurement time can be shortened. The measurement time for the slide 30 ($Na^+$, $K^+$, $Cl^-$ potential difference measurement item) is approximately one minute, whereas the measurement time for the long test film 3 (color reaction) is approximately four minutes on the average. Therefore, in order to shorten the overall measurement time, measurement for the slide 30 should be carried out last. Also, since the sample applying positions 41' and 41" for the slide 30, the nozzle washing region 18, and the sample accommodating means 4 are provided close to one another, the distance of movement of the sample application means 5 between the step of application of the liquid sample to the slide 30 and the step of application of the reference solution to the slide 30 by the aforesaid operations can be minimized, and the overall measurement time can further be shortened.

The slide 30 on which the liquid sample and the reference solution have already been applied is incubated in the manner as mentioned above, and the difference in potential is measured. The measurement results are fed to the computer 20, necessary calculation processing is carried out, and the results of calculation processing are stored and fed out.

After the sample application is finished in the manner as mentioned above, the sample application means 5 is moved to the nozzle washing region 18, and the leading edge 15a of the sample applying nozzle 15 is immersed in distilled water. Thereafter, the pistons 124 and 125 shown in FIG. 8 are moved to their start positions if they were not there, and the liquid sample, the reference solution and the like are delivered from the leading edge 15a of the sample applying nozzle 15. The washing liquid is then accumulated in the cylinder 108 by the above-mentioned operations, and delivered from the leading edge 15a of the sample applying nozzle 15 for the purpose of washing.

In the case where the liquid sample which is to be determined next is still present in the sample accommodating means 4 or the centrifugation means 6 after the aforesaid operations have been finished, the liquid sample is moved to the liquid sample take-out position 40a or 42a, and the aforesaid operations are repeated.

Figure 9:
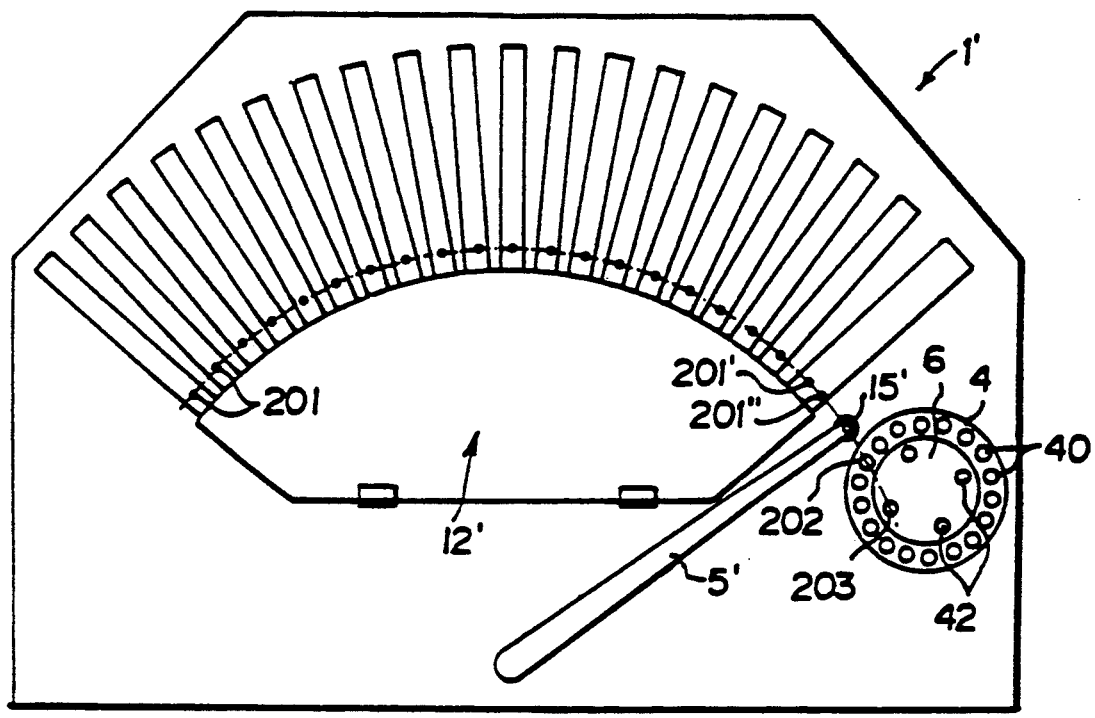
FIG. 9 is a plan view showing another embodiment of the biochemical analysis apparatus in accordance with the present invention.

FIG. 9 shows another embodiment of the biochemical analysis apparatus in accordance with the present invention.

With reference to FIG. 9, a biochemical analysis apparatus 1' is different from the aforesaid apparatus 1 in that a sample applying nozzle 15' of a sample application means 5' is moveable along a circular arc path indicated by the chain line in FIG. 9. Sample applying positions 201, 201' and 202" for all test films pulled or pushed out of a test film accommodating means 12', a liquid sample take-out position 202 of the sample accommodating means 4, and a liquid sample take-out position 203 of the centrifugation means 6 are disposed in the circular arc path.

With the arrangement in the circular arc path, as in the case of the aforesaid embodiment employing the arrangement on the straight line, the configuration of a movement means (not shown) for rotating the sample application means 5' can be simplified, failures of the apparatus 1' can be minimized, and the cost thereof can be reduced.

Figure 10:
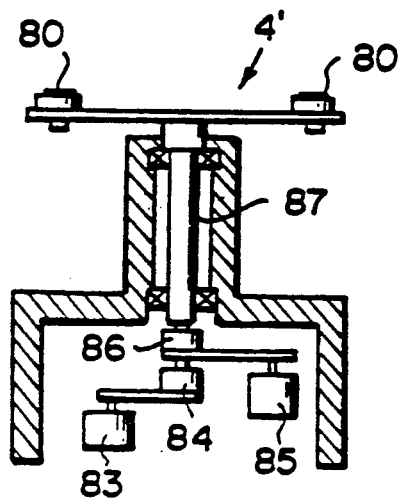
FIG. 10 is a sectional view showing the sample accommodating means provided with a centrifuging function.

FIG. 10 shows a sample accommodating means 4' provided with the centrifuging function.

In the aforesaid embodiment, as shown in FIG. 7, the sample accommodating means 4 is disposed outward from the centrifugation means 6. Instead, in the embodiment shown in FIG. 10, the sample accommodating means 4' accommodates both the liquid sample and the body fluid, and is provided with the centrifuging function for preparing the liquid sample by centrifuging the body fluid accommodated in the sample accommodating means 4'. In FIG. 10, similar elements are numbered with the same reference numerals with respect to FIG. 7. With this embodiment, the configuration becomes simpler, failures of the apparatus can be decreased to a higher extent and the cost thereof can further be reduced than in the case where the sample accommodating means 4 and the centrifugation means 6 are disposed as shown in FIG. 7.

FIG. 11 shows a further embodiment of the biochemical analysis apparatus in accordance with the present invention. In this embodiment, instead of providing a centrifugation means 6' inward from the sample accommodating means 4, an apparatus 1' is constituted so that it is dividable into an analysis unit 204 and a centrifugation unit 205.

By way of example, the analysis unit 204 and the centrifugation unit 205 stand side by side as shown in FIG. 11, the body fluid after centrifugation (liquid sample) is transferred by a sample transfer means 206 from the centrifugation means 6' to the sample accommodating means 4. Transfer of the liquid sample may be carried out by taking up the liquid sample by use of the same configuration as the sample application means 5. Alternatively, sample cups of the same type for containing the liquid sample (body fluid) may be used at the centrifugation means 6' and the sample accommodating means 4, and the liquid sample may be transferred together with the sample cup from the centrifugation means 6' to the sample accommodating means 4.

After the liquid sample has been transferred as mentioned above, measurement is carried out in the same manner as in the case where no liquid sample (body fluid) is placed at the centrifugation means 6 in the aforesaid embodiment.

With the apparatus 1" dividable into the analysis unit 204 and the centrifugation unit 205, in the case where only a liquid sample requiring no centrifugation is to be analyzed or a centrifugal separator is already present, analysis can be carried out by use of the analysis unit 204 alone. Therefore, the apparatus 1" is advantageous from the viewpoint of economics. In the case where the centrifugation unit 205 is provided as shown in FIG. 11, the analysis unit 204 and the centrifugation unit 205 can be operated integrally by the aid of the sample transfer means 206.

The aforesaid embodiments of the biochemical analysis apparatus in accordance with the present invention are constituted for carrying out both the measurement of a change in the optical density by use of the long test film 3 and the measurement of a difference in potential by use of the slide. However, the function of measuring the difference in potential may be provided when necessary, and the biochemical analysis apparatus may be constituted for carrying out only the measurement of a change in the optical density by use of the long test film 3.

It is also possible to constitute the biochemical analysis apparatus for carrying out one of the measurement of a change in the optical density by use of the long test film 3 and the measurement of a difference in potential by use of the slide. Also, in the case where the biochemical analysis apparatus is constituted for carrying out the measurement of a change in optical density, a slide type test film may be employed instead of the long test film 3.

Also, in the aforesaid embodiments, a plurality of items can be measured by accommodating a plurality of the long test films 3. The biochemical analysis apparatus in accordance with the present invention may also be constituted for accommodating only a single long test film 3.

We claim:

1. A biochemical analysis apparatus comprising:
   i) a sample holding means for holding a liquid sample,
   ii) a centrifugation means for receipt of body fluid and preparing a liquid sample by centrifugation of the body fluid,
   iii) a sample transfer means for transferring said liquid sample prepared by said centrifugation means to said sample holding means,
   iv) a test film holding means for holding n a side-by-side arrangement a plurality of rolls of test film capable of reacting with said liquid sample to result in a change,
   v) a test film conveyance means for each of said rolls of test film for sequentially conveying the test film of a roll held in said test film holding means to a predetermined position outside of said test film holding means,
   vi) a sample application means for taking up said liquid sample out of said sample holding means and applying a predetermined amount of said liquid sample onto a said test film conveyed to said predetermined position,
   vii) an incubator for maintaining the sample-applied portion of said test film at said predetermined position at a predetermined temperature for a predetermined time, said incubator including an opening through which said sample application means applies said liquid sample to said test film, and means for preventing air flow between a position inside of said incubator and a position outside of said incubator, said air flow preventing means being reciprocally movable to cover said opening, and
   viii) a detection means for measuring a change in optical density of said sample-applied portion of said test film at said predetermined position based on a reaction product between said sample applied and said test film during or after the passage of said predetermined time, wherein said predetermined position is inside said incubator.

2. An apparatus as defined in claim 1 wherein said test film comprises an elongated tape.

3. An apparatus as defined in claim 2 wherein said test film holding means is constituted to hold a plurality of elongated tapes, said test film conveyance means, said incubator and said detection means are provided to correspond to each of a plurality of said elongated tapes, and a movement means is provided for moving said sample application means to carry out the sample application to the predetermined position on each of a plurality of said elongated tapes.

4. A biochemical analysis apparatus comprising:
   i) a sample holding means for holding a liquid sample,
   ii) a centrifugation means for receipt of body fluid and preparing a liquid sample by centrifugation of the body fluid,
   iii) a test film holding means for holding in a side-by-side arrangement a plurality of rolls of test film capable of reacting with said liquid sample to result in a change,
   iv) a test film conveyance means for each of said rolls of test film for sequentially conveying the test film of a roll held in said test film holding means to a predetermined position outside of said test film holding means,
   v) a sample application means for taking up said liquid sample out of one of said sample holding means and said centrifugation means selectively and applying a predetermined amount of said liquid sample onto said test film conveyed to said predetermined position,
   vi) an incubator for maintaining the sample-applied portion of said test film at said predetermined position at a predetermined temperature for a predetermined time, said incubator including an opening through which said sample application means applies said liquid sample to said test film, and means for preventing air flow between a position inside of said incubator and a position outside of said incubator, said air flow preventing means being reciprocally movable to cover said opening, and
   vii) a detection means for measuring a change in optical density of said sample-applied portion of said test film situated at said predetermined position based on a reaction product between said sample applied and said test film during or after the passage of said predetermined time, wherein said predetermined position is inside said incubator.

5. An apparatus as defined in claim 4 wherein said test film comprises an elongated tape.

6. An apparatus as defined in claim 5 wherein said test film holding means is constituted to hold a plurality of the elongated tapes, said test film conveyance means, said incubator and said detection means are provided to correspond to each of a plurality of said elongated tapes, and a movement means is provided for moving said sample application means to carry out the sample application to the predetermined position on each of a plurality o said elongated tapes.

7. An apparatus as defined in claim 4 wherein said sample application means is provided with a sample applying nozzle moveable along a straight line or a circular arc, and the liquid sample take-out positions at which said liquid sample is taken up by said sample application means and the sample applying position at which said liquid sample is applied onto said test film are disposed on said straight line or said circular arc.

8. An apparatus as defined in claim 4, wherein said sample holding means holds a plurality of the liquid samples in a ring-shaped area, and said centrifugation means the liquid sample prepared thereby on an inner concentric circle from said ring-shaped area.

9. A biochemical analysis apparatus comprising:
   i) a sample holding means for holding a liquid sample and integrally provided with a centrifuging means for receipt of body fluid and preparing a liquid sample by centrifugation of the body fluid,
   ii) a test film holding means for holding a plurality of rolls of test film capable of reacting with said liquid sample to result in a change, iii) a test film conveyance means for each of said rolls of test film for sequentially conveying the test film held in said test film holding means to a predetermined position outside of said test film holding means, iv) a sample application means for taking up said liquid sample out of said sample holding means and applying a predetermined amount of said liquid sample onto said test film conveyed to said predetermined position, v) an incubator for maintaining the sample-applied portion of said test film at said predetermined position at a predetermined temperature for a predetermined time, said incubator including an opening through which said sample application means applies said liquid sample to said test film, and means for preventing air flow between a position inside of said incubator and a position outside of said incubator, said air flow preventing means being reciprocally movable to cover said opening, and vi) a detection means for measuring a change in optical density of said sample-applied portion of said test film situated at said predetermined position based on a reaction product between said sample and said test film during or after the passage of said predetermined time, wherein said predetermined position in inside said incubator.

10. An apparatus as defined in claim 9, wherein said test film has a comprises an elongated tape.

11. An apparatus as defined in claim 10, wherein said test film holding means is constituted to hold a plurality of elongated tapes, said test film conveyance means, said incubator and said detection means are provided to correspond to each of a plurality of said elongated tapes, and a movement means is provided for moving said sample application means to carry out the sample application to the predetermined position on each of a plurality of said elongated tapes.

12. An apparatus as defined in claim 12 wherein said sample application means is provided with a sample applying nozzle moveable along a straight line or a circular arc, and the liquid sample take-out position at which said liquid sample is taken up by said sample application mans and the sample applying position at which said liquid sample is applied onto said test film are disposed on said straight line or said circular arc.

* * * * *